United States Patent [19]

Makkee

[11] Patent Number: 5,053,571

[45] Date of Patent: Oct. 1, 1991

[54] REDUCTIVE ALKYLATION PROCESS

[75] Inventor: Michiel Makkee, Vlaardingen, Netherlands

[73] Assignee: Exxon Chemical Patents Inc., Linden, N.J.

[21] Appl. No.: 511,912

[22] Filed: Apr. 16, 1990

Related U.S. Application Data

[63] Continuation of Ser. No. 340,326, Apr. 19, 1989, abandoned.

[30] Foreign Application Priority Data

Apr. 19, 1988 [GB] United Kingdom ............... 8809214

[51] Int. Cl.$^5$ .................................................. C07C 2/02
[52] U.S. Cl. .................................................. 585/425
[58] Field of Search ............................... 585/268, 425

[56] References Cited

U.S. PATENT DOCUMENTS

| 4,093,671 | 6/1978 | Murtha et al. | 585/268 |
| 4,094,918 | 6/1978 | Murtha et al. | 585/268 |
| 4,118,434 | 10/1978 | Murtha et al. | 585/268 |
| 4,122,125 | 10/1978 | Murtha et al. | 585/268 |
| 4,177,164 | 12/1979 | Murtha et al. | 502/73 |
| 4,177,166 | 12/1979 | Murtha et al. | 502/73 |
| 4,206,082 | 6/1980 | Murtha et al. | 502/73 |
| 4,268,699 | 5/1981 | Murtha et al. | 585/427 |

FOREIGN PATENT DOCUMENTS

| 197712 | 12/1977 | U.S.S.R. | 585/425 |
| 0443588 | 12/1977 | U.S.S.R. | 585/425 |

Primary Examiner—Curtis R. Davis
Attorney, Agent, or Firm—Edward F. Sherer

[57] ABSTRACT

A monocycloalkyl aromatic hydrocarbon, e.g. cyclohexyl benzene, or a substituted monocycloalkyl aromatic hydrocarbon is prepared by a hydroalkylation process in which respectively an aromatic hydrocarbon, e.g. benzene, or an alkyl substituted aromatic hydrocarbon is contacted with hydrogen in the presence of a catalyst comprising ruthenium and nickel supported on zeolite beta. Optionally the catalyst can also include a rare earth metal, e.g. lanthanum.

13 Claims, No Drawings

REDUCTIVE ALKYLATION PROCESS

This is a continuation of application Ser. No. 340,326, filed Apr. 19, 1989, now abandoned.

This invention relates to a process of reductive alkylation.

Alkylated benzene can be prepared from benzene by the process of reductive alkylation (hydroalkylation). In this process benzene is heated, preferably in the liquid state, with hydrogen under pressure over a certain catalyst, the result of which is that benzene is partially hydrogenated to cyclohexene and this cyclohexene then alkylates the benzene starting material.

Certain catalysts for such reductive alkylation processes have been disclosed, for example ruthenium and nickel compounds supported on a calcined, acidic, rare earth treated crystalline zeolite as disclosed in U.S. Pat. No. 4,122,125 and U.S. Pat. No. 4,206,082. In those specifications type X and type Y zeolites are suggested for use as the substrate. We have surprisingly found that far greater conversions are achieved if the substrate which is used is zeolite beta. Often the use of one of the comparatively expensive rare earth compounds is not necessary.

According to this invention a monocycloalkyl aromatic hydrocarbon or a substituted monocycloalkyl aromatic hydrocarbon is prepared by a process which comprises contacting respectively an aromatic hydrocarbon or an alkyl substituted aromatic hydrocarbon with hydrogen in the presence of a catalyst comprising ruthenium and nickel supported on zeolite beta. This invention also includes monocycloalkyl aromatic hydrocarbons and substituted monocycloalkyl aromatic hydrocarbons made by this process.

The aromatic hydrocarbon starting material is preferably benzene and the alkyl substituted aromatic hydrocarbon starting material is preferably an alkyl substituted benzene. Although in principle any alkyl substituent can be present it is preferred that any alkyl substituent has 1 to 10 carbon atoms, especially 1 to 5 carbon atoms. The most preferred alkyl substituent is methyl. There may be one or more alkyl substituents on the aromatic nucleus. Examples of suitable alkyl substituted aromatic hydrocarbons include toluene, ethyl benzene, the xylenes, trimethyl benzenes and tetra methyl benzenes, such as durene.

It is preferred that the hydrogen is contacted with the aromatic hydrocarbon or alkyl substituted aromatic hydrocarbon under pressure and pressures of between 100 and 2000, e.g. between 100 and 600 kPa, are usually suitable.

The catalyst comprises ruthenium and nickel supported on zeolite beta. In practice, the catalyst is made by treating zeolite beta with a ruthenium compound and a nickel compound by ion-exchange, impregnation or incipient wetness techniques. Although the zeolite beta may initially contain the ruthenium and nickel in the form of ruthenium and nickel compounds, during the reductive alkylation conditions the compounds are decomposed and the actual catalyst contains ruthenium and nickel in metallic form.

Zeolite beta is described and claimed in U.S. Pat. No. 3,308,069, reissued as Re 28341 where it is described as a crystalline synthetic material whose composition has been calculated to be:

where x is less than 1, preferably less than 0.75; TEA represents tetraethylammonium ion; y is from 5 to 100 and w is from 0 to 4 depending on the condition of dehydration and on the metal cation present. The TEA component is calculated on the basis of the difference between the analyzed value of sodium and the ultimate theoretical cation to Al ration of 1.0/1.

Zeolite beta is also described as a form of a crystalline synthetic material which has catalytic properties having the composition:

where x, y and w have the values listed above and n is the valence of the metal M which can be any metal, preferably a metal of groups IA, IIA, IIIA or the transition metals of the periodic table.

This form of the catalyst is obtained from the initial sodium form of zeolite beta by ion exchange. Zeolite beta is described as being formed by crystallization from a reaction mixture containing the tetraethylammonium ion. Upon heating of the product, at a temperature in the approximate range of 200°-930° C. or higher, the tetraethylammonium ion undergoes degradation to the hydrogen ion. Furthermore, in this case the value of w in the formula may be essentially 0.

The zeolite beta is described as being prepared from reaction mixtures containing tetraethylammonium hydroxide as the alkali and more specifically by heating in aqueous solution a mixture of the oxides or of materials whose chemical compositions can be completely represented gas mixtures of the oxides $Na_2O$, $Al_2O_3$, $[(C_2H_4)_4N]_2O$, $SiO_2$ and $H_2O$ at a temperature of 75° C. to 200° C. until crystallization occurs. The composition of the prior art reaction mixture, expressed in terms of mole ratios, preferably falls within the following ranges:

$SiO_2/Al_2O_3$—from 10 to 200.

$Na_2O$/tetraethylammonium hydroxide (TEAOH)—from 0.0 to 0.1.

$TEAOH/SiO_2$—from 0.1 to 1.0.

$H_2O/TEAOH$—from 20 to 75.

Zeolite beta can be made by a method comprising reacting in aqueous media, amorphous silica solids or sols and a soluble aluminate along with aqueous solutions of tetraethylammonium hydroxide. The aluminate may be sodium aluminate or tetraethylammonium aluminate. Amorphous silica-alumina solids may be used as the source of the silica and alumina. The reaction mixture is initially continuously or periodically stirred to ensure homogeneity. After this mixing, agitation may be stopped as it is unnecessary to agitate the reaction mass during the formation and crystallization of the zeolite, although mixing during such latter stages has not been found to be detrimental.

Zeolite beta may also be made by the process of EP-A-0187522 in which a reaction mixture comprising sources of sodium, aluminium, TEA, silicon and water and having the following molar ratios of components (expressed in terms of oxides):

$SiO_2/Al_2O_3$ = 10–200, preferably 10–100,
$Na_2O/TEA_2O$ = 0.3–1.0, preferably 0.3–0.8.
$TEA_2O/SiO_2$ = 0.01–0.1, preferably 0.05–0.1, -continued H₂O/TEA₂O = 25-150, preferably 40-100, is heated at a temperature of at least 75° C. until zeolite beta is formed.

In a preferred aspect, particularly for small scale preparations, the reaction mixture is formed by first mixing powdered sources of sodium oxide, silica and alumina, optionally with zeolite beta seeds, and without the addition of any substantial amount of water and thereafter combining the mixed powder with an aqueous solution containing TEA cations.

The source of silica for use in the process of EP-A-0187522 is preferably an amorphous solid silica, dry silicic acid or a silicate. The source of alumina may be alumina itself, or an aluminate such as sodium aluminate, in which latter case the aluminate also acts as a source of some or all of the sodium. Alternatively a silica-alumina solid may be used as the source of both the silica and alumina. Sodium may be added in the form of any sodium compound provided that the anion thus introduced does not interfere with the synthesis. Apart from sodium aluminate, a preferred sodium source is sodium hydroxide. These sources optionally together with preformed zeolite beta seeds are mixed, e.g. in a mill, in the first step to form a mixed powder.

The source of TEA cations for the aqueous solution used in the second stage of the preparation of the reaction may be tetraethylammonium hydroxide or a salt, provided that the anion does not interfere with the zeolite formation.

The crystallization can be carried out at temperatures of at least 75° C. and generally in the range of 100° C. to 250° C. The crystallization time is dependent of the reaction mixture and the crystallization temperature, generally of the order of 2 to 20 days. The pressure during crystallization may be atmospheric or greater, e.g. varying from 1 to 60 bar. Crystallization is conveniently carried out under autogeneous conditions.

After formation, zeolite beta may be separated from the mother liquor and washed using normal work-up techniques.

The zeolite beta used in the process of this invention includes not only the sodium form of zeolite beta as synthesized from a system with sodium as the exchangeable cation but also crystalline materials obtained from such a zeolite by partial or complete replacement of the sodium ion with other cations. The sodium cations can be replaced, at least in part, by other ions including but not limited to those of metals below sodium in the electromotive series, calcium, ammonium, hydrogen and mixtures thereof. Particularly preferred for such purpose are the alkaline earth metal ions; transition metal ions such as manganese and nickel; rare earth metal ions and other ions, for example, hydrogen and ammonium which behave in zeolite beta as metals in that they can replace ions without causing any appreciable change in the basic structure of the zeolite crystal.

The zeolite can be used immediately after calcining in air without any further treatment or the zeolite can be subjected to ion exchange after calcining but before the use. Preferred ions for the exchange include: $Li^+$, $K^+$, $Cs^+$, $Mg^{++}$, $Ca^{++}$, $Sr^{++}$, $Ba^{++}$, $La^{3+}$, and $Ce^{3+}$ especially $Cs^+$ and $K^+$. Preferably the amount of ions exchanged onto the sieve is as much as can be loaded onto the sieve.

When using the ion-exchange technique to form the catalyst, aqueous solutions of the ruthenium and nickel compounds are used and the concentrations can be varied over wide ranges, but usually the concentrations range up 2 to 5 weight percent.

Zeolite beta is treated with the aqueous solution of ruthenium and nickel compounds to replace a portion of either the alkali metal or other cation content of the zeolite in a cation exchange process which can be carried out in a batch or continuous fashion. Generally, the exchange process is carried out on a continuous basis under the following typical conditions. A fixed bed of the zeolite material is treated with said aqueous solution of ruthenium and nickel compounds at a temperature of 60° to 100° C. under conditions such that from about 0.1 to about 0.5 of the volume of aqueous salts solution per volume of zeolite is in contact with said zeolite per hour or, in other words, an LHSV ranging from about 0.1 to about 0.5 is employed in the exchange process. Under these conditions, the exchange process can be completed in 48 hours or less to achieve the desired level of ruthenium and nickel cations in the zeolite. The exchanged zeolite is then washed free of excess ions from the exchange step with water. The excess wash water is removed by drying the zeolite at a temperature ranging from 100° to 250° C.

In the impregnation technique the zeolite beta is impregnated with a solution of at least one ruthenium compound and at least one nickel compound followed by evaporation of the solvent used in the impregnation step. Solutions of the ruthenium and nickel compounds may be used and the concentrations can be varied over a wide range, but usually the concentrations range from 0.1 to 25 weight per cent. Evaporation of the solvent can be conducted under vacuum if desired. Suitable solvents include water, alcohols, such as ethanol, and ketones, such as acetone.

The impregnation is generally carried out under what may be called "total impregnation" whereby the entire solids in the solutions used in the impregnation are left on the catalyst support and the liquid solvent for said compounds is simply removed by evaporation.

In the incipient wetness technique, the zeolite beta is soaked under reduced pressure with a solution of at least one ruthenium compound and at least one nickel compound in order just to fill the pores and channels of the zeolite. As with the impregnation technique the concentrations of nickel and ruthenium compounds can vary over a wide range, but usually the concentrations range from 0.1 to 25 weight per cent. The excess of solution left over in the zeolite beta channels may be removed by drying the zeolite beta at temperatures of between about 100° C. and about 250° C.

Under the above described conditions, the ion exchange and impregnation processes can be completed in 48 hours or less to achieve the desired level of uniform dispersion of ruthenium and nickel cations in the beta zeolite.

In all these techniques of treating the zeolite beta with ruthenium and nickel compounds, various ruthenium and nickel compounds can be employed such as the nitrates, acetates, halides, e.g. chlorides or ammonium halide complexes or ammonium nitrate complexes. Particularly preferred are the chlorides because of cost and availability. It is preferred that the above-mentioned loading techniques be carried out with a mixture of the ruthenium and nickel compounds although the tre⁻ ing can be carried out with the separate compounds in either order as long as the desired level of ruthenium and nickel is achieved in the final catalyst composition.

The ruthenium content and nickel content in the final catalyst composition can be selected over a broad range. Generally, the ruthenium content ranges from 0.01 to 3 percent by weight. Good results can be obtained employing a ruthenium content within the range of from 0.5 to 1.5, e.g. about 1.0 percent by weight. These same ranges also apply for the nickel content of the final product. However, for improved catalytic activity, the nickel ruthenium weight ratio in the final catalyst should be in the range of from 1:10 to 10:1, preferably in the range of from 1:2 to 2:1.

If desired, the zeolite beta may be impregnated or otherwise treated with a rare earth compound, preferably before it is treated with the ruthenium and nickel compounds. Treatment can be by the methods described above, and the preferred method is ion exchange. Various rare earth compounds may be used, e.g. a chloride, of for example cerium, neodymium or in particular lanthanum. In general the amounts of rare earth salts used should be such as to produce 1 to 5, e.g. 2 to 4 or about 3 weight percent rare earth in the final catalyst.

It is also found that the inclusion of tungsten with ruthenium and nickel on zeolite beta improves the activity of the catalytic system, but with lower selectivity to the desired monocyclo alkyl aromatic hydrocarbon. Tungsten may be incorporated in the catalyst by the methods described above and the final catalyst should preferably contain 0.1 to 5.0 weight %, e.g. about 0.5 weight % of tungsten.

The catalyst containing the compounds of ruthenium and nickel and optionally tungsten and rare earth are preferably activated by reduction. This reduction is preferably carried out by subjecting the catalyst to an atmosphere of hydrogen at a temperature of 50° to 600° C., at a pressure of from 1 to 2000 kPa and for 15 minutes to 24 hours. Alternatively air may be used instead of hydrogen.

The reductive alkylation (hydroalkylation) occurs through the partial hydrogenation of the aromatic hydrocarbon to a cyclo alkene. The cyclo alkene then reacts with the aromatic hydrocarbon or alkyl substituted aromatic hydrocarbon to obtain the desired monocycloalkyl aromatic hydrocarbon or substituted monocycloalkyl aromatic hydrocarbon.

To carry out the reaction the feedstock, that is the aromatic hydrocarbon or alkyl substituted aromatic hydrocarbon, is introduced into a reaction zone comprising the catalyst. The feedstock liquid hourly space velocity (LHSV), reaction temperature and pressure, and the hydrogen feed rate are not particularly critical. The liquid hourly space velocity (LHSV) generally ranges from 1 to 100, the reaction pressure generally ranges from 100 to 1000 kPa, the hydrogen feed rate generally ranging from 0.2 to 6 mole per mole of feedstock per hour, and the reaction temperature generally ranging from 100° to 300° C. In particular it is preferred to use a liquid hourly space velocity (LHSV) within the range of from 5 to 25, a reaction pressure within the range of from 100 to 600 kPa with a hydrogen feed rate of from 0.2 to 6 mole per mole of feedstock per hour, and the reaction temperature within the range of from 100° C. to 250° C.

The hydroalkylation reaction is conveniently carried out by having the above-described catalyst in a fixed bed reactor and then contacting said catalyst with the hydrocarbon feedstock and hydrogen in an upflow or downflow arrangement. It is also possible to employ a countercurrent flow of hydrogen and the hydrocarbon feedstock over the catalyst in the reaction zone. It is also possible to carry out the hydroalkylation reaction under batch conditions, although a batch process is less preferred because it is normally more expensive to operate and initial equipment costs are higher based upon the same size process.

Although a fixed bed reactor is mentioned above, any type of reaction zone can be used.

The reaction mixture from the reaction zone can usually be conveniently separated into the desired components by simple fractional distillation and recycle of the unreacted feedstock and unreacted hydrogen can be accomplished as desired. The hydroalkylation products can be further purified as desired after separation from unreacted feedstock.

The process of this invention is particularly suitable for the preparation of cyclohexyl benzene from benzene.

Cyclohexyl benzene can be used as a solvent, starting material for detergents or processed in two steps to cyclohexanone and phenol (nylon precursors).

The invention is now illustrated by the following Examples:

EXAMPLE 1

Benzene was hydroalkylated in 8 different runs. Runs 1,2 and 3 were carried out using a catalyst according to the invention (zeolite beta made by the process of EP-A-0187522) and runs 4 to 8 were comparative runs using different catalysts (sodium form of zeolite Y, mordenite or no nickel present).

In each run, which was a batch hydroalkylation, 200 ml of predried benzene were contacted with 1 g of catalyst in a reactor at 200° C. Hydrogen was introduced into the reactor and maintained at a pressure of 550 kPa. The catalyst was prepared by two different techniques, namely an ion-exchange and incipient wetness.

The results are given in Table 1 which indicates the $SiO_2/Al_2O_3$ ratio, the reaction time, the conversion of benzene and the selectivity. It can be seen that catalysts based on zeolite beta have much superior properties in comparison with other supports. It can be seen that the combination of ruthenium and nickel is better than ruthenium alone on zeolite beta since the addition of nickel enhances the selectivity to cyclohexylbenzene. It can be noted that the addition of tungsten to ruthenium and ruthenium and nickel on zeolite beta improves the activity of the catalyst but at the expense of selectivity to cyclohexylbenzene.

TABLE 1

| | | | Hydroalkylation of Benzene | | | | | |
| | | | | Reaction | Conversion | | Selectivity (%)[b] | |
| | | | Preparation[a] | Time | of Benzene | | | |
| Exp. | Catalyst | $SiO_2/Al_2O_3$ | Technique | (hr) | (%) | Cx | Cx= CyhexBz | R |
| 1 | 1% Ru-0.5% Ni-Beta | 51 | IW | 2.0 | 22.7 | 30.0 | <0.1   70.0 | ≤0.1 |

TABLE 1-continued

Hydroalkylation of Benzene

| Exp. | Catalyst | $SiO_2/Al_2O_3$ | Preparation[a] Technique | Reaction Time (hr) | Conversion of Benzene (%) | Selectivity (%)[b] | | | |
|---|---|---|---|---|---|---|---|---|---|
| | | | | | | Cx | Cx= | CyhexBz | R |
| 2 | 1% Ru-1.0% Ni-Beta | 51 | IW | 1.0 | 36.9 | 29.3 | <0.1 | 65.1 | 5.6 |
| 3 | 1% Ru-0.5% Ni-0.5% W-Beta | 51 | IW | 2.0 | 45.7 | 62.8 | <0.1 | 37.2 | <0.1 |
| 4 | 3% Ru-NaY | 4–5 | IE | 1.0 | 41.6 | 79.1 | 0.7 | 20.2 | <0.1 |
| 5 | 1% Ru-Mordenite | 72 | IE | 2.0 | 25.3 | 71.3 | <0.1 | 28.7 | <0.1 |
| 6 | 1% Ru-Mordenite | 114 | IW | 2.0 | 19.4 | 75.4 | <0.1 | 24.6 | <0.1 |
| 7 | 1% Ru-Beta | 28 | IE | 1.0 | 98.6 | 82.4 | <0.1 | 12.0 | 4.6 |
| 8 | 1% Ru-0.5% W-Beta | 51 | IW | 2.0 | 91.0 | 81.4 | <0.1 | 18.6 | <0.1 |

[a]Preparation technique: IE = ion exchange; IW = incipient wetness method.
[b]Selectivities are based on weight yields and defined as amount of product/amount of converted benzene Cx = cyclohexane; Cx= = cyclohexene; CyhexBz = cyclohexylbenzene; R = total amount of byproducts.

EXAMPLE 2

In this Example benzene was hydroalkylated in 8 different runs. Runs 1 to 4 were runs according to the invention and runs 5 to 8 were comparative runs using different catalysts (Linde SK 500 and either no ruthenium or no nickel).

In each run which was a batch hydroalkylation 100 ml of predried benzene were contacted with 0.5 g of catalyst for 1 hour at a temperature of 200° C. and under a pressure of 550 kPa of hydrogen. The catalysts were prepared by the incipient wetness technique followed by 4 hours drying at 120° C.

Before using each catalyst it was activated either by heating under an atmosphere of hydrogen or under an atmosphere of air, in both cases at 400° C. and for 4 hours.

The results are shown in Table 2 from which it can be seen from a comparison of runs 2 and 6 how the use of zeolite beta is superior to that of zeolite Y. Although runs 1 and 2 show a slightly inferior performance to runs 7 and 8 concerning selectivity to cyclohexyl benzene the process of this invention (runs 1 and 2) does not require the use of the relatively expensive rare earth metal lanthanum. However, if one does use lanthanum then better results are achieved by the present invention (using zeolite beta) (runs 3 and 4) than by a prior art process (using Linde SK 500) runs 7 and 8. It is also noted that the activation of the catalyst with hydrogen gives better results as regards selectivity towards cyclohexyl benzene than the activation of the catalyst with air (run 1 vs. run 2, run 3 vs. run 4, and run 7 vs. run 8).

TABLE 2

Hydroalkylation of Benzene

| Run | Catalyst | $SiO_2/Al_2O_3$ | Activation Method | Benzene Conversion (%) | Selectivity (%)[a] | | | |
|---|---|---|---|---|---|---|---|---|
| | | | | | Cx | Cx= | CyhexBz | R |
| 1 | 1% Ru-1% Ni-Beta | 51 | $H_2$/400° C. | 36.9 | 29.3 | <0.1 | 65.1 | 5.6 |
| 2 | 1% Ru-1% Ni-Beta | 51 | Air/400° C. | 41.7 | 58.8 | 0.9 | 36.7 | 3.6 |
| 3 | 1% Ru-1% Ni-3% La-Beta | 51 | $H_2$/400° C. | 25.8 | 16.6 | <0.1 | 77.3 | 6.1 |
| 4 | 1% Ru-1% Ni-3% La-Beta | 51 | Air/400° C. | 56.9 | 29.2 | <0.1 | 68.4 | 2.5 |
| 5 | 1% Ni-3% La-Y (Y = Linde SK 500) | n.a. | Air/400° C. | 8.7 | 83.9 | <0.1 | 12.6 | 3.4 |
| 6 | 1% Ru-1% Ni-Y (Y = Linde SK 40) | n.a. | Air/400° C. | 38.8 | 96.1 | 2.1 | 1.0 | 0.7 |
| 7 | 1% Ru-1% Ni-3% La-Y | n.a. | $H_2$/400° C. | 19.3 | 25.6 | <0.1 | 70.3 | 4.1 |
| 8 | 1% Ru-1% Ni-3% La-Y (Y = Linde SK 500) | n.a. | Air/400° C. | 39.3 | 39.9 | 0.3 | 57.8 | 1.5 |

[a]Selectivities are based on weight yields and defined as amount of product/amount of converted benzene Cx = cyclohexane; Cx= = cyclohexene; CyhexBz = cyclohexylbenzene; R = total amount of byproducts.
n.a. = not available

I claim

1. A process for preparing a monocycloalkyl aromatic hydrocarbon or a substituted monocycloalkyl aromatic hydrocarbon which comprises contacting respectively an aromatic hydrocarbon or an alkyl substituted aromatic hydrocarbon with hydrogen in the presence of a catalyst comprising ruthenium and nickel supported on zeolite beta.

2. A process according to claim 1 wherein the aromatic hydrocarbon is benzene

3. A process according to claim 1 wherein the hydrogen is under a pressure of between 100 and 2000 kPa.

4. A process according to claim 1 wherein the weight percent of ruthenium is from 0.01 to 3 and that of nickel between 0.01 and 3.

5. A process according to claim 1 wherein the catalyst also includes 1 to 5 weight percent of rare earth metal(s).

6. A process according to claim 1 wherein the catalyst also includes 0.1 to 3.0 weight percent of tungsten.

7. A process according to claim 1 wherein the catalyst has been activated by subjecting it to an atmosphere of hydrogen at a temperature of 50 to 600° C., at a pressure of from 1 to 2000 kPa for 15 minutes to 24 hours.

8. A process according to claim 7 wherein the hydrogen is maintained at a pressure of from 100 to 1000 kPa.

9. A process according to claim 7 wherein the reaction temperature is between 100° C. and 300 C.

10. A process according to claim 1, said zeolite beta being first treated with a rare earth compound and being subsequently treated with ruthenium and nickel compounds.

11. A process according to claim 1 wherein the catalyst includes a rare earth metal, said zeolite beta having first been treated with a rare earth compound.

12. A process according to claim 11 wherein said rare earth compound is a chloride.

13. A process according to claim 12 wherein said chloride is selected from a group consisting of cerium chloride, neodymium chloride and lanthanum chloride.

* * * * *